United States Patent
Ueda et al.

[11] 3,950,374
[45] Apr. 13, 1976

[54] CARBAMATE PESTICIDE

[75] Inventors: Minoru Ueda, Takarazuka; Shigehiro Ooba, Kobe; Masachika Hirano, Toyonaka; Hisami Takeda, Takarazuka, all of Japan

[73] Assignee: Sumitomo Chemical Company, Limited, Osaka, Japan

[22] Filed: Jan. 23, 1973

[21] Appl. No.: 326,101

[30] Foreign Application Priority Data
  Jan. 26, 1972 Japan .............................. 47-10155
  Mar. 7, 1972 Japan .............................. 47-23700

[52] U.S. Cl. ...... 260/453 R; 260/471 C; 260/479 C; 260/481 C; 424/298; 424/300
[51] Int. Cl.² .............................. C07C 119/18
[58] Field of Search ......... 260/453 R, 470; 424/303

[56] References Cited
UNITED STATES PATENTS

| | | | |
|---|---|---|---|
| 2,927,126 | 3/1960 | Pursglove | 71/103 |
| 3,576,834 | 4/1971 | Buchanan | 260/453 R |
| 3,624,257 | 11/1971 | Sakai et al. | 424/303 |
| 3,663,594 | 5/1972 | Brown et al. | 71/98 |
| 3,712,913 | 1/1973 | Subraya et al. | 260/470 |
| 3,766,172 | 10/1973 | Phillips | 71/98 |
| 3,825,579 | 7/1974 | Fujimoto et al. | 260/453 R |

FOREIGN PATENTS OR APPLICATIONS
7,005,795  10/1970  Netherlands .................. 260/453 R OTHER PUBLICATIONS
Biasotti et al., "Hydrolysis of Arenesulfinamides etc.;" (1970).
JACS 93 pp. 1178–1182 (1971).

Primary Examiner—Glennon H. Hollrah
Attorney, Agent, or Firm—Wenderoth, Lind & Ponack

[57] ABSTRACT

Compounds of the formula

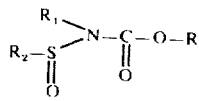

wherein R is phenyl, α-naphthyl, substituted phenyl or a group of the formula

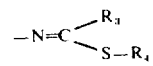

$R_1$ is lower alkyl, $R_2$ is alkyl, phenyl, aralkyl or substituted phenyl, and $R_3$ and $R_4$ are lower alkyl, which compounds are useful as insecticidal, nematocidal and acarididal agents.

3 Claims, No Drawings

CARBAMATE PESTICIDE

The present invention relates to new insecticidal, nematocidal and acaricidal compositions characterized by containing new carbamate compounds as active ingredients and their preparation.

More particularly, the present invention (1) relates to new insecticidal, nematocidal and acaricidal compositions characterized by containing one or more of new carbamate compounds having the general formula (I) mentioned below as an active ingredient. In other words, it is an object of the invention to provide pesticides which make it possible to control injurious insects economically by displaying their full activity as contact poison, stomach poison, smoke poison and nerve poison directly or indirectly against injurious insects, mites and nematodes.

The new carbamate compounds according to the invention have the following general formula (I):

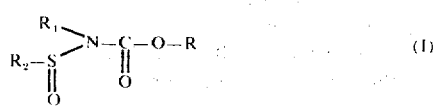

wherein

R represents a phenyl, α-naphthyl, a substituted phenyl of the general formula:

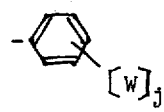

wherein W represents a lower $C_1 - C_4$ alkyl, lower $C_1 - C_4$ alkoxyl, lower $C_1 - C_4$ alkylthio, lower di $C_1 - C_4$ alkylamino, nitro or halogen, $j$ represents an integer from 1 to 5, and all W's need not necessarily be the same, or a group of the general formula:

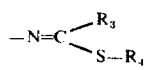

wherein $R_3$ and $R_4$ represent a lower $C_1 - C_4$ alkyl and may be the same or different, $R_1$ represents an lower $C_1 - C_5$ alkyl and $R_2$ represents an alkyl, phenyl, aralkyl of the general formula:

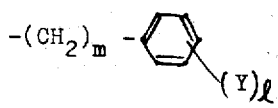

or a substituted phenyl of the general formula:

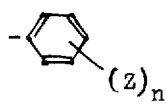

wherein Y represents a hydrogen atom, lower $C_1 - C_4$ alkyl, lower $C_1 - C_4$ alkoxyl, lower $C_1 - C_4$ alkylthio, nitro or halogen, $l$ and $m$ represent an integer from 1 to 3, Z represents lower $C_1 - C_4$ alkyl, lower $C_1 - C_4$ alkoxyl, lower $C_1 - C_4$ alkylthio, halogen, nitro or trihalomethyl, $n$ represents an integer from 1 to 5 and all Z's need not necessarily be the same.

The compounds according to the invention can advantageously be used for controlling insects which are injurious to agriculture, forests as well as insects which are injurious to the household, because they are extremely active against not only injurious insects which belong to Hemiptera, Diptera, Lepidoptera, Orthoptera and the like, but also plant-parasitic nematodes and mites. Particularly, the compounds according to the invention exhibit quick and strong insecticidal activity against mosquito larvae and Hemiptera insects such as planthoppers, leafhoppers, aphids, bugs and the like. Since these Hemiptera insects not only cause direct harm to plants, but also act as a vector of plant virus such as rice dwarf disease and rice striped disease, the compounds according to the invention can also be said to have a controlling effect on plant disease.

Moreover, the compounds according to the invention exhibit strong insecticidal activity against larvae of Lepidoptera such as tobacco cut worms, cabbage worms, cut worms and rice stem borer, and have also activity against resistant injurious insects.

Although the compounds according to the invention, as explained above, exhibit strong insecticidal, nematocidal and acaricidal activities, their toxicity to warm-blooded animals is very low and consequently can safely be employed without any phytotoxicity in a practical concentration. The compounds can be applied with an excellent controlling effect by means of spraying and dusting as well as soil treatment.

Now, the compounds according to the invention can optionally be formulated, in the same manner as in common insecticides, into various forms of preparation such as emulsifiable concentrates, wettable powders, dusts, oil sprays, granules, fine granules, coatings and bait by the methods well known to those skilled in the art, and can be applied in any form as desired.

Furthermore, the compounds according to the invention can also be formulated into multi-purpose compositions by mixing with other active ingredients, for example, organophosphorus insecticides including Sumithion (a trademark of Sumitomo Chemical Company, Limited, Japan; o,o-dimethyl-o-(3-methyl-4-nitrophenyl)-phosphorothioate), Malathion, Dimetoate, Salithion (a trademark of Sumitomo Chemical Company, Limited, Japan; 2-methoxy-4H-1,3,2-benzodioxophosphorin-2-sulfide), Surecide (a trademark of Sumitomo Chemical Company, Limited, Japan; o-ethyl-o-(4-cyanophenyl)phenylphosphonothioate), Cyanox (a trademark of Sumitomo Chemical Company, Limited, Japan; o,o-dimethyl-o-(4-cyanophenyl)phosphorothioate), Baycid, DDVP and EPN, organo-chlorine insecticides including BHC, DDT, Drin (polychlorinated hydrocarbon) and Chlordane, carbamate insecticides including Meobal (a trademark of Sumitomo Chemical Company, Limited, Japan; 3,4-dimethylphenyl-N-methylcarbamate), m-tolyl-N-methylcarbamate, 2-sec.-butylphenyl-N-methylcarbamate, S-methyl-N[(methylcarbamoyl)oxy]-thioacetoimidate, 1-naphthyl-N-methylcarbamate and the like, pyrethroid insecticides including Pyrethrin, Allethrin and the like, acaricides, nematocides, fungicides, herbicides, plant regulators, fertilizers, soil disinfectants and other analogues. Thus, by the use of the present compounds in combination with the active ingredients as mentioned above, the excellent activity thereof is surely displayed and the synergistic effect can also be expected.

The present invention (1) has been accomplished on the basis of the new knowledge described above.

The present invention (2) relates to the method for preparing the compounds, more particularly to the method for preparing the compounds of the general formula (I) in a high yield,

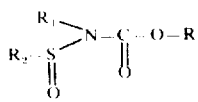  (I)

by reacting a sulfinylhalide of the general formula (II);

  (II)

wherein $R_2$ has the same meanings as defined above and X represents a halogen atom, with an N-alkylcarbamic acid ester of the general formula (III);

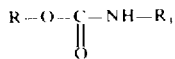  (III)

wherein R and $R_1$ have the same meanings as defined above, in the presence or absence of suitable organic solvents, for example, benzene, toluene, xylene, ether, chloroform or carbon tetrachloride at −10° to 50°C, in the presence or absence of suitable hydrogen halide-binding agents, for example, tertiary amines including triethylamine, N,N-diethylaniline, N,N-dimethylaniline, pyridine, N-methylmorphorine and the like.

The typical examles of sulfinylhalides and N-alkylcarbamates which are employed according to the present invention will be illustrated hereinafter, but they are, of course, not limitative thereto.

Sulfinylhalides:

wherein Z represents a chlorine, bromine or iodine atom, and $R_2$ represents a methyl, ethyl, n-propyl, iso-propyl, butyl, pentyl, hexyl, octyl, decyl, lauryl, phenyl, 4-nitrophenyl, 4-chlorophenyl, 4-trifluoromethylphenyl, 2-bromophenyl, 2-methyl-4-propylphenyl, 2,4-dichlorophenyl, 4-methylphenyl, 3,4-dimethylphenyl, 4-ethylphenyl, 2,4,5-trichlorophenyl, 2-nitrophenyl, 4-methoxyphenyl, 4-methylthiophenyl, benzyl, 4-chlorobenzyl, 4-ethylbenzyl, 2-butylbenzyl, 4-methoxybenzyl, 4-methylthiobenzyl, 4-nitrobenzyl, phenethyl, phenylpropyl, 3,5-dichlorophenyl, 2-ethylphenyl or 4-isopropylphenyl.

N-Alkylcarbamates:

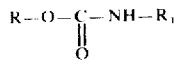

wherein $R_1$ represents methyl, ethyl, propyl, butyl or pentyl, and R represents a phenyl, 3-n-propylphenyl, 3-iso-propylphenyl, 3-sec.-butylphenyl, 3-tert.-butylphenyl, 3-methyl-5-sec.-butylphenyl, 3-n-propyl-5-sec.-butylphenyl, 3-amylphenyl, 3-methylphenyl, 3-ethyl-5-methylphenyl, 3,4-dimethylphenyl, 2,4-dimethylphenyl, 3,5-dimethylphenyl, 4-methylphenyl, 4-chlorophenyl, 4-isopropylphenyl, 4-butylphenyl, 2,4-dichlorophenyl, 2,4,6-trichlorophenyl, 4-bromophenyl, 3,5-dibromophenyl, 2-chloro-5-tert.-butylphenyl, 2-sec.-butylphenyl, 2-iso.-propylphenyl, 2-nitrophenyl, 3-methyl-4-nitrophenyl, 4-methoxyphenyl, 4-methylthiophenyl, or the compounds of the general formula:

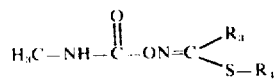

wherein $R_3$ and $R_4$ each represents a methyl, ethyl, n-propyl, iso.-propyl, n-butyl, sec.-butyl or tert.-butyl radical.

The typical examples of carbamate compounds of the general formula (I) prepared by the method above described will be illustrated hereinafter which are, of course, not limitative thereto.

| Compound No. | Chemical structure |
|---|---|
| 1 | ![structure] |
| 2 | ![structure] |
| 3 | ![structure] |
| 4 | ![structure] |
| 5 | ![structure] |
| 6 | ![structure] |
| 7 | ![structure] |

| Compound No. | Chemical structure |
|---|---|
| 8 | H₃C–⌬(CH₃)–O–C(=O)–N(CH₃)–S(=O)(=O)–⌬–CH₃ |
| 9 | H₃C,CH₃–⌬–O–C(=O)–N(CH₃)–S(=O)(=O)–⌬–CH₃ |
| 10 | H₃C–⌬(CH₃)–O–C(=O)–N(CH₃)–S(=O)(=O)–⌬–NO₂ |
| 11 | H₃C–⌬(CH₃)–O–C(=O)–N(CH₃)–S(=O)(=O)–⌬–Cl |
| 12 | H₃C–S(=O)(=O)–N(CH₃)–C(=O)–O–N=C(CH₃)(S–CH₃) |
| 13 | (n–)H₅–C₂–S(=O)(=O)–N(CH₃)–C(=O)–O–N=C(CH₃)(S–CH₃) |
| 14 | H₂₅C₁₂–S(=O)(=O)–N(CH₃)–C(=O)–O–N=C(CH₃)(S–CH₃) |
| 15 | ⌬–S(=O)(=O)–N(CH₃)–C(=O)–O–N=C(CH₃)(S–CH₃) |
| 16 | Cl–⌬–S(=O)(=O)–N(CH₃)–C(=O)–O–N=C(CH₃)(S–CH₃) |
| 17 | H₃C–⌬–S(=O)(=O)–N(CH₃)–C(=O)–O–N=C(CH₃)(S–CH₃) |
| 18 | O₂N–⌬–S(=O)(=O)–N(CH₃)–C(=O)–O–N=C(CH₃)(S–CH₃) |
| 19 | ⌬–S(=O)(=O)–N(CH₃)–C(=O)–O–N=C(C₂H₅)(S–CH₃) |
| 20 | H₃C₂–S(=O)(=O)–N(CH₃)–C(=O)–O–N=C(C₂H₅)(S–C₂H₅) |
| 21 | Cl–⌬–S(=O)(=O)–N(CH₃)–C(=O)–O–N=C(CH₃)(S–C₃H₇(n)) |

The present invention will be illustrated in more detail with reference to the following examples.

EXAMPLE 1

17.9 g. (0.1 mol) of 3,4-dimethylphenyl-N-methyl-carbamate and 100 ml. of pyridine are placed in a 200 ml. flask with four necks and then 19.5 g. (0.1 mol) of 4-chlorophenylsulfinyl chloride are added thereto while cooling. The mixture is stirred at room temperature for 4 hours, poured into ice, and then a separated aqueous layer is extracted twice with chloroform. The chloroform extract is washed with water, dried over anhydrous sodium sulfate and then chloroform is removed under reduced pressure to give an amide carbamate compound of the formula,

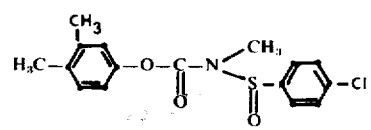

Yield 90 %, m.p. 75° – 76°C.

Elemental analysis:

|  | C % | H % | N % | S % |
|---|---|---|---|---|
| Calculated | 56.88 | 4.78 | 4.15 | 9.49 |
| Found | 57.05 | 4.68 | 4.32 | 9.26 |

The following compounds are obtained in a similar manner as described in Example 1.

| Chemical structure | Yield (%) | Physical constant | | C (%) | H (%) | N (%) | S (%) |
|---|---|---|---|---|---|---|---|
| Cl–⌬–O–C(=O)–N(CH₃)–S(=O)–⌬–Cl | 89 | m.p. 102°C. | Calculated | 48.85 | 3.23 | 4.07 | 9.31 |
|  |  |  | Found | 48.60 | 3.14 | 3.94 | 9.35 |

| Chemical structure | Yield (%) | Physical constant | Elemental analysis | C (%) | H (%) | N (%) | S (%) |
|---|---|---|---|---|---|---|---|
| 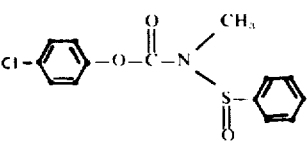 | 92 | m.p. 86–88°C | Calculated | 54.26 | 3.91 | 4.52 | 10.35 |
| | | | Found | 54.17 | 3.92 | 4.59 | 10.11 |
| 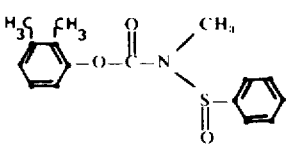 | 91 | m.p. 57–59°C | Calculated | 63.34 | 5.66 | 4.62 | 10.57 |
| | | | Found | 63.28 | 5.65 | 4.61 | 10.28 |
| 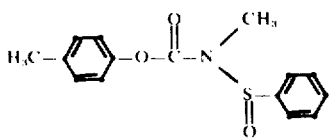 | 93 | m.p. 76°C | Calculated | 63.34 | 5.66 | 4.62 | 10.57 |
| | | | Found | 63.26 | 5.71 | 4.59 | 10.32 |
| 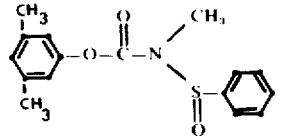 | 95 | m.p. 74–75°C | Calculated | 63.34 | 5.66 | 4.62 | 10.57 |
| | | | Found | 63.50 | 5.77 | 4.60 | 10.76 |
| 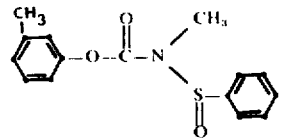 | 90 | $n_D^{20.5}$ 1.5778 | Calculated | 62.26 | 5.24 | 4.84 | 11.08 |
| | | | Found | 61.92 | 5.11 | 4.91 | 11.00 |
| 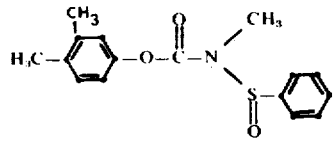 | 88 | $n_D^{25.0}$ 1.5774 | Calculated | 63.34 | 5.66 | 4.62 | 10.57 |
| | | | Found | 63.20 | 5.69 | 4.49 | 10.32 |
| 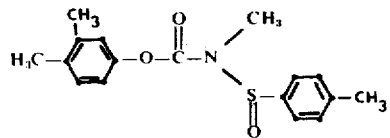 | 91 | $n_D^{24.0}$ 1.5788 | Calculated | 64.32 | 6.05 | 4.41 | 10.10 |
| | | | Found | 64.36 | 5.91 | 4.37 | 10.13 |
| 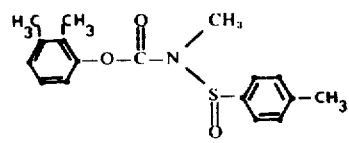 | 90 | m.p. 83–85°C | Calculated | 64.32 | 6.05 | 4.41 | 10.10 |
| | | | Found | 64.10 | 6.19 | 4.26 | 9.87 |
| 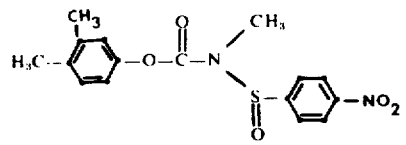 | 93 | m.p. 129–130°C | Calculated | 55.15 | 4.63 | 8.06 | 9.20 |
| | | | Found | 55.06 | 4.75 | 8.11 | 9.18 |

EXAMPLE 2

16.2 g. (0.1 mol) of S-methyl-N[(methylcarbamoyl)-oxy] thioacetoimidate and 100 ml. of pyridine are placed in a flask with four necks and then 16.1 g. (0.1 mol) of phenylsulfinyl chloride are added thereto while cooling. The mixture is stirred at room temperature for 4 hours, poured into ice, and then a separated aqueous layer is extracted twice with chloroform. The chloroform extracts are washed with water, dried over anhydrous sodium sulfate and the chloroform is removed under reduced pressure to give an amide carbamate compound of the formula:

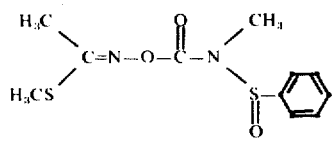

Yield 91 %, m.p. 72° – 75°C.

| Elemental analysis: | | | | |
|---|---|---|---|---|
| | C % | H % | N % | S % |
| Calculated | 46.13 | 4.94 | 9.78 | 22.39 |
| Found | 45.93 | 4.76 | 9.66 | 22.15 |

The following compounds are obtained in a similar manner as described in Example 1.

| Structure | | | |
|---|---|---|---|
| H₃C\C=N—O—C(=O)—N(CH₃)—S(=O)₂—C₆H₄—Cl / H₃CS | Yield | 93 % | |
| | m.p. | 117 – 120°C. | |
| H₃C\C=N—O—C(=O)—N(CH₃)—S(=O)₂—C₆H₄—NO₂ / H₃CS | Yield | 96 % | |
| | m.p. | 143 – 143.5°C. | |
| H₃C\C=N—O—C(=O)—N(CH₃)—S(=O)₂—C₆H₄—CH₃ / H₃CS | Yield | 87 % | |
| | m.p. | 140 – 142°C. | |
| H₃C\C=N—O—C(=O)—N(CH₃)—S(=O)₂—CH₃ / H₃CS | Yield | 95 % | |
| | $n_D^{18}$ | 1.5436 | |

The composition according to the invention is illustrated with reference to the following preparation examples.

PREPARATION 1

25 parts by weight of compound (1) of the invention, 30 parts by weight of DMF, 25 parts by weight of cyclohexanone and 20 parts by weight of Sorpol 2020 (a trademark of Toho Chemical Co., Ltd., Japan) are mixed thoroughly in this order to make a uniform emulsifiable concentrate. The emulsifiable concentrate is diluted with water and then applied.

PREPARATION 2

40 parts by weight of compound (2) of the invention, 10 parts by weight of Tokusil GO-N (a trademark of Tokuyama Soda Co., Ltd., Japan), 45 parts by weight of Radiolite (a tradename of Showa Kagaku Co., Ltd., Japan) and 5 parts by weight of Sarpol 5029 (a trademark of Toho Chemical Co., Ltd., Japan) are mixed thoroughly to make 40 % wettable powder. The wettable powder is diluted with water and then applied.

PREPARATION 3

5 parts by weight of compound (3) of the invention and 95 parts by weight of talc are mixed thoroughly and pulverized to make 5 % dust. The dust is applied as such.

PREPARATION 4

3 parts by weight of compound (4) of the invention, 2 parts by weight of sodium ligninsulfonate and 95 parts by weight of 200 mesh clay are mixed thoroughly in this order, kneaded with a small amount of water, granulated by means of a granulator and then dried to make 3 % granules. The granules are applied as such.

PREPARATION 5

25 parts by weight of compound (12) of the invention, 30 parts by weight of DMF, 25 parts by weight of cyclohexanone and 20 parts by weight of Sorpol 2020 (a trademark of Toho Chemical Co., Ltd., Japan) are mixed thoroughly in this order to make a uniform emulsifiable concentrate. The emulsifiable concentrate is diluted with water and then applied.

PREPARATION 6

40 parts by weight of compound (17) of the invention, 10 parts by weight of Tolusil CO-N (a trademark of Tokuyama Soda Co., Ltd., Japan), 45 parts by weight of of Radiolite (a tradename of Showa Kagaku Co., Ltd., Japan) and 5 parts by weight of Sorpol 5029 (a trademark of Toho Chemical Co., Ltd., Japan) are mixed thoroughly to make 40 % wettable powder. The wettable powder is diluted with water and then applied.

PREPARATION 7

5 parts by weight of compound (16) of the invention and 95 parts by weight of talc are mixed thoroughly and pulverized to make 5 % dust. The dust is applied as such.

PREPARATION 8

3 parts by weight of compound (15) of the invention, 2 parts by weight of sodium ligninsulfonate and 95 parts by weight of 200 mesh clay are mixed thoroughly in this order, kneaded with a small amount of water, granulated by means of a granulator and then dried to make 3 % granules. The granules are applied as such.

TEST EXAMPLE 1

Lethal effect on smaller brown planthoppers (*Laodelphax striatellus*)

Rice plants (15 to 20 cm tall) 15 days after germination, are dipped for 1 minute into each aqueous dilute solution of the present compounds in the form of emulsifiable concentrates, and placed in large glass tubes separately after air-drying. Thereafter, 20 to 30 adult planthoppers are released therein and covered with a wire net. After 24 hours, the number of dead and live planthoppers are observed to calculate $LC_{50}$. The results are as shown in Table 1. The number of the compounds in Table 1 correspond to those of the compounds mentioned above.

Table 1

| Compound No. | $LC_{50}$ (ppm) |
|---|---|
| 2 | 20 |
| 3 | 70 |
| 4 | 33 |
| 5 | 18 |
| 6 | 25 |
| 7 | 43 |
| 8 | 50 |
| 9 | 29 |
| 10 | 33 |
| 11 | 40 |
| 15 | 123 |
| 16 | 151 |

TEST EXAMPLE 2

Effect on smaller brown planthoppers (*Laodelphax striatellus*) in soil treatment.

Each of 6 % granules of the present compounds is applied in a ratio of 6 kg./10 ares near the root of rice plants grown into the tillering stage a 1/100,000 Wagner's pot. After 3 days, 30 adult planthoppers are released and covered with a wire cage. After 24 hours, the number of dead and live planthoppers are observed to calculate the mortality rate. The results are shown in Table 2.

Table 2

| Compound No. | Mortality (%) |
|---|---|
| 12 | 85.0 |
| 14 | 90.0 |
| 15 | 89.7 |
| 16 | 72.4 |
| 20 | 66.7 |

TEST EXAMPLE 3

Effect on green peach aphids (*Myzus persicae*) in soil treatment.

Many of the aphids are made parasitic on chinese cabbages grown in a pot one month after sowing, and each of 5 % granules of the present compounds is applied in a ratio of 6 kg./10 ares near the root thereof. After 3 days, the number of dead and live aphids are observed to calculate the mortality rate. The results are as shown in Table 3.

Table 3

| Compound No. | Mortality (%) |
|---|---|
| 12 | 87.3 |
| 13 | 96.7 |
| 14 | 76.5 |
| 15 | 95.9 |
| 16 | 100 |
| 18 | 68.8 |

TEST EXAMPLE 4

Effect on green rice leafhoppers (*Nephotettix cincticeps*) in soil treatment.

Each of 6 % granules of the present compounds is applied in a ratio of 6 kg./10 ares near the root of rice plants grown into the tillering stage in a 1/100,000 Wagner's pot. After 3 days, 30 adult leafhoppers are released and covered with a wire cage. After 24 hours, the number of dead and live leafhoppers are observed to calculate the mortality rate. The results are as shown in Table 4.

Table 4

| Compound No. | Mortality (%) |
|---|---|
| 2 | 75.0 |
| 5 | 68.0 |
| 7 | 96.7 |
| 9 | 83.3 |
| 10 | 72.2 |
| 15 | 70.0 |
| 16 | 89.3 |

TEST EXAMPLE 5

Lethal effect on rice stem borer (*Chilo suppressalis*).

Eggs just before hatching of the rice stem borer are applied in a ratio of 100/pot near the root of rice plants grown into the tillering stage in a 1/100,000 Wagner's pot. After the eggs hatched and the larvae enter into stems of rice plants, a 1000 fold dilute solution of each 50 % emulsifiable concentrate of the present compounds is applied by means of a turn table. The number of dead and live stem borers are observed to calculate the mortality rate 4 days after application. The resuls are shown in Table 5.

Table 5

| Compound No. | Mortality (%) |
|---|---|
| 12 | 95.0 |
| 13 | 83.2 |
| 15 | 82.3 |
| 16 | 94.9 |
| 17 | 76.5 |
| 19 | 66.7 |

TEST EXAMPLE 6

Effect on nematode.

0.5 ml. of a nematode-containing aqueous solution separated from food is placed in a test tube with ground stopper containing 0.5 ml. of an aqueous dilute solution of each emulsifiable concentrate of the present compounds. The concentration of the active ingredient in the mixture is adjusted to 500 ppm. After 24 hours, the number of dead and live nematodes are observed microscopically to calculate the mortality rate. The results are as shown in Table 6.

Table 6

| Compound No. | Mortality (%) |
| --- | --- |
| 2 | 79.8 |
| 6 | 100 |
| 11 | 75.0 |
| 12 | 100 |
| 13 | 100 |
| 14 | 100 |
| 15 | 100 |
| 16 | 94.8 |
| 17 | 100 |
| 18 | 100 |
| 21 | 65.0 |

TEST EXAMPLE 7

Effect on tobacco cut worm (*Spodoptera litura*).

A 1000 fold dilute solution of each emulsifiable concentrate of the present compounds is applied by means of a turn table to a potted chinese cabbage 60 days after sowing. After air-drying, fourth instar larvae of the tobacco cut worm are released and the mortality rate after 24 hours and 48 hours is calculated. The results are as shown in Table 7.

Table 7

| Compound No. | Mortality (%) | |
| --- | --- | --- |
| | After 24 hrs. | After 48 hrs. |
| 12 | 80 | 95 |
| 13 | 100 | 100 |
| 14 | 90 | 100 |
| 15 | 80 | 90 |
| 16 | 70 | 75 |
| 17 | 80 | 85 |
| 18 | 70 | 85 |

TEST EXAMPLE 8

Effect on mosquito larvae.

200 ml. of an aqueous solution of each emulsifiable concentrate of the present compounds which is adjusted to the concentration of 1 ppm with pure water are placed in a 300 ml. beaker and 30 larvae of northern house mosquito (*Culex pipien pallens*) are released therein. the mortality rate is calculated. The results are as shown in Table 8.

Table 8

| Compound No. | Mortality (%) |
| --- | --- |
| 6 | 70.0 |
| 8 | 100 |
| 9 | 66.7 |
| 11 | 100 |
| 15 | 78.3 |
| 16 | 100 |

TEST EXAMPLE 9

Effect on tabacco cut worm (*Spodoptera litura*).

A field of chinese cabbage, 40 days after sowing, is divided into areas of 99 m.² and 3 % granules of the present compound (15) are applied in a ratio of 3 kg./990 m.². Then eggs of the tobacco cut worm are made parasitic, in a ratio of 300 eggs/3.3 m.², on leaves of chinese cabbage every 5 days for a month. The generation of the tobacco cut worm is never observed in the field for 2 months until harvest time.

TEST EXAMPLE 10

Acaricidal activity on carmine mite (*Tetranychus telarius*).

From 10 to 15 female carmine mites are made parasitic, in a ratio of 10 – 15/leaf, on leaves of potted kidney beans is (a leaves stage), 9 days after sowing, and kept at 27°C. For a week in a constant temperature room, then breeding of numerous carmine mites at various growth stages can be observed. At this time, a 1000 fold aqueous dilute solution of each 40 % wettable powder of the present compounds is sprayed by means of a turn table in a ratio of 10 ml./pot. After 10 days, the degree of damage of kidney beans and the degree of breeding of mites are observed and classified into five grades (−, +, 30 +, +++, ++++). The results are as shown in Table 9.

The degree of damage of kidney bean leaves:
−; damage is hardly observed,
++++; leaves are dead,
and the degree of damage in between the two extremes is classified into three grades.

The degree of breeding of carmine mites: − ; the number alive is less than 10,
++++; the alive are numerous.
and the degree of breeding in between the two extremes is classified into three grades.

Table 9

| Compound No. | Degree of damage | Degree of breeding |
| --- | --- | --- |
| 12 | + | + |
| 15 | −−+ | −− |
| 16 | −−+ | −−+ |
| 17 | + | +−++ |
| No treatment | ++++ | ++++ |

TEST EXAMPLE 11

Residual effect on smaller brown planthoppers (*Loadelphax striatellus*).

From 18 to 23 rice plants are grown into a 3 – 4 leaves stage in each flower pot of 10 cm. in diameter, then a 1000 fold aqueos dilute solution of each 50 % emulsifiable concentrate of the present componds is applied thereto. After air-drying, each pot is covered with a wire cage, and 20 – 30 adult planthoppers are released therein, and after 24 hours the mortality rate is calculated. Furthermore, the planthoppers are released each day to investigate the residual effect of the present compounds. The results are as shown in Table 10.

Table 10

| Compound No. | Mortality (%) | | |
| --- | --- | --- | --- |
| | after 1 day | after 4 days | after 7 days |
| 2 | 96.7 | 75.0 | 20.0 |
| 3 | 100 | 64.0 | 50.0 |
| 4 | 100 | 83.3 | 53.3 |
| 5 | 100 | 100 | 45.0 |
| 6 | 90.0 | 63.3 | 50.0 |
| 7 | 86.7 | 65.0 | 46.7 |
| 8 | 85.0 | 50.0 | 42.0 |
| 9 | 100 | 62.3 | 30.0 |
| 10 | 100 | 50.0 | 23.3 |
| 11 | 100 | 85.0 | 75.0 |
| Standard Meobal | 100 | 53.2 | 10.0 |
| No treatment | 3.3 | 0 | 9.6 |

What we claim is:

1. A compound of the formula
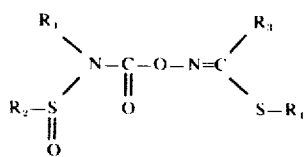
wherein $R_1$ represents alkyl of 1 to 5 carbon atoms, $R_2$ represents alkyl of 1 to 12 carbon atoms, phenyl or phenyl monosubstituted by methyl, nitro o chloro, and $R_3$ and $R_4$ are the same or different alkyl of 1 to 4 carbon atoms.
2. Compound of the formula
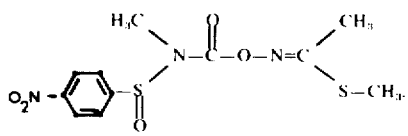
3. Compound of the formula
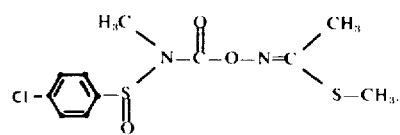
* * * * *